US007122692B2

(12) United States Patent
Plehiers et al.

(10) Patent No.: US 7,122,692 B2
(45) Date of Patent: Oct. 17, 2006

(54) PROCESS FOR THE PREPARATION OF ORGANOSILYLATED CARBOXYLATE MONOMERS, AND THEIR USE IN ANTIFOULING COATINGS

(75) Inventors: Mark Plehiers, Brussels (BE); Marcel Vos, Nivelles (NL); Michel Gillard, Louvain-la-Neuve (BE)

(73) Assignee: Sigma Coatings B.V., Uithoorn (NL)

( * ) Notice: Subject to any disclaimer, the term of this patent is extended or adjusted under 35 U.S.C. 154(b) by 68 days.

(21) Appl. No.: 10/490,126

(22) PCT Filed: Sep. 19, 2002

(86) PCT No.: PCT/EP02/10552

§ 371 (c)(1),
(2), (4) Date: Sep. 3, 2004

(87) PCT Pub. No.: WO03/027124

PCT Pub. Date: Apr. 3, 2003

(65) Prior Publication Data

US 2005/0014963 A1 Jan. 20, 2005

(30) Foreign Application Priority Data

Sep. 21, 2001 (EP) ................... 01203581
Apr. 19, 2002 (EP) ................... 02076553

(51) Int. Cl.
*C07F 7/02* (2006.01)
*C07F 7/04* (2006.01)
*C07F 7/08* (2006.01)
*C07F 7/18* (2006.01)

(52) U.S. Cl. ............... 556/439; 556/442; 556/438; 556/440; 556/437; 556/436; 556/453; 556/456; 524/432; 523/122; 526/279

(58) Field of Classification Search .......... 556/439, 556/442, 438, 440, 437, 436, 453, 456; 524/432; 523/122; 526/279
See application file for complete search history.

(56) References Cited

U.S. PATENT DOCUMENTS 4,593,055 A   6/1986   Gitlitz et al.
4,594,365 A   6/1986   Russell et al.
4,957,989 A   9/1990   Saitoh
6,063,887 A   5/2000   Okawa

FOREIGN PATENT DOCUMENTS

| EP | 0 297 505 A2 | 1/1989 |
|----|---|---|
| EP | 0 775 733 A1 | 5/1997 |
| EP | 0 714 957 B1 | 3/1998 |
| EP | 1016681 A2 | 7/2000 |
| EP | 0 802 243 B1 | 5/2001 |
| EP | 1127902 A1 | 8/2001 |
| EP | 1127925 A1 | 8/2001 |
| JP | 03-118381 | 5/1984 |
| JP | 63-215780 | 9/1986 |
| JP | 01-132668 | 5/1989 |
| JP | 01-145969 | 6/1989 |
| JP | 05-077712 | 3/1993 |
| JP | 05-306290 | 11/1993 |
| JP | 07-018215 | 1/1995 |
| JP | 10-245451 | 5/1998 |
| JP | 10195084 A2 | 7/1998 |
| WO | WO 84/02915 | 6/1984 |

OTHER PUBLICATIONS

"Encyclopedia of Polymer Science and Engineering", Mark HF et al., 2nd ed., John Wiley & Sons (1989), vol. 15, p. 207 et seq.
XP-002190781, Anderson et al., Ethylsilicon Esters And Transesterifications, Contribution From The Chemistry Department, Drexel Institute of Technology, (1953), pp. 1716-1719.
XP 002190782, Kozuka et al., Kinetic Studies for the Acyloxy Exchange Reactions of Acyloxytrimethylsilanes With Caroboxylic Acids, Bulletin Of The Chemical Society of Japan vol. 52 (7) 1950, 1952 (1979) pp. 1950-1952.
A. Chapman & A. D. Jenkins, J. Polym. Sci. Polym. Chem. Edn. vol. 15, p. 3075 (1977).
H. H. Anderson et al., J. Org. Chem. 1296 (1954).
Izv. Akad. Nauk. Ussr. Ser. Khim. 968 (1957).

*Primary Examiner*—Elvis O. Price
(74) *Attorney, Agent, or Firm*—Goodwin Procter LLP

(57) ABSTRACT

Process for the preparation of organosilylated carboxylate monomers comprising the step of reacting an acyloxysilane with an unsaturated carboxylic acid, the monomers and their use as comonomer unit in the binder of antifouling coating compositions.

14 Claims, No Drawings

PROCESS FOR THE PREPARATION OF ORGANOSILYLATED CARBOXYLATE MONOMERS, AND THEIR USE IN ANTIFOULING COATINGS

CROSS REFERENCE TO RELATED PATENT APPLICATIONS

This is a national phase filing of International Application No. PCT/EP02/10552, which was filed with the Patent Corporation Treaty on Sep. 19, 2002, and is entitled to priority of European Patent Application No. 01203581.2 filed Sep. 21, 2001 and European Patent Application No. 02076553.3 filed Apr. 19, 2002.

FIELD OF THE INVENTION

The invention relates to a new method for the preparation of organosilylated carboxylate monomers. The invention further relates to said obtained organosilylated carboxylate monomers and in another aspect, the invention further relates to their use for the synthesis of hydrolysable polymers, such as binders for modern antifouling coatings.

BACKGROUND

Antifouling paints are used to prevent and delay the fouling of underwater structures (e.g. ships' bottom, docks, fishnets, and buoys) by various marine organisms such as shells, seaweed, and aquatic bacteria. When such marine organisms adhere and propagate on an underwater structure like the bottom of a ship, the surface roughness of the whole ship may be increased to induce decrease of velocity of the ship or increase of fuel consumption. Further, removal of such aquatic organisms from the ship's bottom needs much labour and a long period of working time. In addition, if these organisms adhere and propagate on an underwater structure such as a steel structure they deteriorate their anticorrosive coating films leading to a reducing of the lifetime of the underwater structure.

Underwater structures are therefore coated with antifouling paint employing polymers containing various hydrolysable groups and more specifically organosilyl groups.

EP 0297505 relates to an antifouling paint that contains a polymer having organosilyl groups and/or organopolysiloxane groups in side chains. Since the organopolysiloxane group is derived from dehydrating condensation or like means of silicon oil with methacrylic acid, this patent refers to a mixture of oligomers having different numbers of the recurrence of the organosiloxane group.

Another patent JP 10245451 A describes a mixture of organosilylated carboxylate oligomers having different numbers of the recurrence of the organosiloxane group in acrylic rubber composition.

WO 8402915 and JP 63215780 A describe an antifouling paint of the hydrolysable self-polishing type employing a methacrylic ester polymer having triorganosilyl group in side chains or a similar polymer. Other examples of patents and patent applications related to the use of organosilyl acrylate polymers in antifouling compositions are EP 131626, U.S. Pat. No. 4,593,055, 4,594,365, JP 63118381 A, EP 0775733, WO 9638508, JP 11116257 A, EP 802243, EP 0714957, JP 07018216 A, JP 01132668 A, JP 05077712 A, JP 01146969 A and U.S. Pat. No. 4,957,989 and hereby incorporated by reference.

Some of the polymers used in the above-described antifouling paints are based on silylated carboxylate monomers.

Several processes are known as conventional techniques for the synthesis of said silylated carboxylate monomers.

JP 5306290 A describes a process to obtain a methacrylic functional group-containing organosilicon compound. The process comprises reacting methacrylic acid with a halogenoalkylsilane (e.g. trialkylsilylchloride) in the presence of a tertiary amine compound having a cyclic structure. This process has disadvantages such as the reduced availability and storage stability of the silyl chloride. Moreover, the reaction yields as a by-product a hydrogen halide (which provokes the corrosion of the production equipment) or a halide salt (which has to be removed by filtration).

The synthesis of trimethylsilyl methacrylate from methacrylic acid and hexamethyldisilazane is described in A. Chapman & A. D. Jenkins J. Polym. Sci. Polym. Chem. Edn. vol 15, p. 3075 (1977).

JP 10195084 A discloses the reaction of unsaturated carboxylic acid such as acrylic acid or methacrylic acid with a trialkylsilylhydride compound in the presence of a copper catalyst. One of the disadvantages of this method is the risk of hydrogenation of the unsaturated carboxylic acid due to a side reaction of the produced H2 on the carbon-carbon double bond.

Trialkylsilylcarboxylates of aliphatic carboxylic acids can be obtained by transesterification. H. H. Anderson et al. describe in J. Org. Chem 1716 (1953) the reactions of triethyl silyl acetates with halogenated propionic acids and in J. Org. Chem. 1296 (1954) the reactions of trifluoro silyl acetates or propionates with chloroacetic acid; they distil the acetic or propionic acid under reduced pressure.

Russian chemists (Izv. Akad. Nauk. Ussr. Ser. Khim. 968 (1957)) run similar reactions at much higher temperatures (190–210° C.).

JP 95070152 A discloses reactions of trialkylsilylacetates with C6 to C30 carboxylic acids (e.g. palmitic, myristic, benzoic, . . . ); the acetic acid is distilled under reduced pressure or azeotropically with hexane.

S. Kozuka et al. in Bull. Chem. Soc. Jap. 52 (7) 1950 (1979) study the kinetics of acyloxy exchange reaction between acyloxysilanes and carboxylic acids. The rate of the reaction has been found to proceed faster with a stronger attacking acid and a more basic leaving acyloxy group.

An object of the present invention is to provide a novel process capable of readily preparing organosilylated carboxylate monomers in a high yield from easily available starting materials.

Another object of the present invention is to provide a more direct method for the synthesis of such organosilylated carboxylate monomers, with easy work-up procedures.

A further object of the present invention is to provide a novel process offering an improvement vis-à-vis of the disadvantages disclosed above.

The present invention is based on the use of unsaturated carboxylic acids with acyloxysilanes to synthesize organosilylated carboxylate monomers. The use of unsaturated carboxylic acids in this reaction was unexpected as it is well known by the man of the art that the unsaturated carboxylic acids are polymerisable and lead to very low rate of reaction.

The present inventor has surprisingly found that by reacting acyloxysilanes with unsaturated carboxylic acids weaker than the leaving acyloxy group, organosilylated carboxylate monomers could be synthesised.

SUMMARY OF THE INVENTION

The present invention relates to a new process for the preparation of organosilylated carboxylate monomers of general formula (I)

$$R^7-CH=C\begin{matrix}R^6\\ \\C-O\\\parallel\\O\end{matrix}\left(\begin{matrix}R^4\\|\\Si-O\\|\\R^5\end{matrix}\right)_n\begin{matrix}R^1\\|\\Si-R^2\\|\\R^3\end{matrix} \quad (I)$$

wherein $R^1$, $R^2$, $R^3$, $R^4$, $R^5$ each independently represent an alkyl, an aryl group or a hydrogen atom, $R^6$ represents a hydrogen atom or a methyl group or —$CH_2$—COO—$(SiR^4R^5O)_n$-$SiR^1R^2R^3$ wherein $R^1$, $R^2$, $R^3$, $R^4$, $R^5$ are as already defined, $R^7$ represents a hydrogen atom, an alkyl group or —$COOR^9$ wherein $R^9$ represents an alkyl group, n represents a number of dihydrocarbylsiloxane units from 0 to 200, which process comprises the steps of reacting:

an acyloxysilane of formula (II)

$$R^8\begin{matrix}\\C-O\\\parallel\\O\end{matrix}\left(\begin{matrix}R^4\\|\\Si-O\\|\\R^5\end{matrix}\right)_n\begin{matrix}R^1\\|\\Si-R^2\\|\\R^3\end{matrix} \quad (II)$$

wherein $R^1$, $R^2$, $R^3$, $R^4$ and $R^5$ are as already defined above and, $R^8$ is a hydrogen atom, a $C_1$–$C_3$ alkyl group, a partially or totally hydrogenated $C_1$–$C_3$ alkyl group, n represents the same number of dihydrocarbylsiloxane units as those defined above in formula (I), with an unsaturated carboxylic acid of formula (III), $$R^7-CH=C\begin{matrix}R^6\\ \\C-OH\\\parallel\\O\end{matrix} \quad (III)$$

wherein $R^6$ is a hydrogen atom or a methyl group or $CH_2COOH$ and, $R^7$ has the same meaning as that defined above.

According to one preferred embodiment of the process of the invention, n in formulas (I) and (II) equals zero.

According to another preferred embodiment, n in formulas (I) and (II) represents a number of dihydrocarbylsiloxane units from 1 to 200.

In a preferred embodiment $R^1$, $R^2$, $R^3$, $R^4$, $R^5$ and $R^9$ each independently represent a linear, branched, cyclic alkyl, aryl or substituted aryl group, saturated or unsaturated, containing from 1 to 12 carbon atoms, preferably from 1 to 6 carbon atoms, more preferably from 1 to 4 carbon atoms, yet more preferably 4 carbon atoms. More preferably, $R^1$, $R^2$, $R^3$, $R^4$, $R^5$ each independently are chosen from the group of methyl, ethyl, propyl, isopropyl, i-butyl, n-butyl, sec-butyl, t-butyl. In a more preferred embodiment $R^1$, $R^2$, $R^3$ are n-butyl or isopropyl and n equals zero. In another more preferred embodiment $R^1$ to $R^5$ are methyl and n is not zero.

In another embodiment when $R^7$ is —$COOR^9$, the organosilylated carboxylates of general formula (I) and the unsaturated carboxylic compound (III) can be of either cis (maleic) or trans (fumaric) configuration.

The process of the invention enables to obtain organosilylated carboxylate monomers with exactly the desired number of the dihydrocarbylsilyloxane units.

According to one preferred embodiment, the organosilylated carboxylates obtained by the process of the invention have a number of dihydrocarbylsiloxane units (n) equal to 0.

According to another preferred embodiment, the organosilylated carboxylates obtained by the process of the invention have a number of dihydrocarbylsiloxane units (n) from 1 to 200, preferably from 1 to 19, more preferably from 1 to 4.

In a more preferred embodiment the organosilylated carboxylates obtained by the process of the invention are organosilyl acrylates or organosilyl methacrylates.

In yet a more preferred embodiment, when organosilyl methacrylates with n equals 1 are obtained by the process of the invention, not all of $R^1$ to $R^5$ are methyl.

DETAILED DESCRIPTION OF THE INVENTION

The present invention relates to a new process for the synthesis of organosilylated carboxylates according to the general scheme:

$$R^7-CH=C(R^6)COOH + \quad (III)$$
$$R^8-COO-(SiR^4R^5-O)_n-SiR^1R^2R^3 \longrightarrow \quad (II)$$
$$R^7-CH=C(R^6)COO-(Si^4R^5-O)_n-SiR^1R^2R^3 + R^8COOH \quad (I)$$

Unsaturated carboxylic acids represented by the above formula (III) are mixed with acyloxysilane (II) with or without solvent. The reaction is preferably set up in such a way that each mole of acyloxysilane is treated with at least one mole of unsaturated carboxylic acid. Examples of solvent which can be used in the process according to the invention include hexane, toluene, xylene, N,N-dimethylformamide, N-methylpyrrolidone, N,N-dimethylacetamide and mixtures thereof. A preference is given for a solvent that causes no distillation of any of the reactants. A much-preferred solvent is a solvent making a low boiling azeotrope with the distilled acid. The reaction may be conducted with or without added polymerisation inhibitor. The reaction progress may be monitored by any suitable analytical method as well as with the determination of the amount of acid distilled.

Examples of unsaturated carboxylic acids which can be used in the process according to the invention include acrylic acid, methacrylic acid, crotonic acid, angelic acid, tiglic acid, maleic acid, fumaric acid, itaconic acid (methylenesuccinic acid), acrylic acid and methacrylic acid, and the mono-esters of the diacids, such as e.g. mono-butyl maleate, mono-ethyl fumarate.

The acyloxysilanes of general formula $R^8$—COO—$(SiR^4R^5$—$O)_n$—$SiR^1R^2R^3$ which can be used in the process according to the invention are derived from carboxylic acids R$^8$—COOH having a boiling point of maximum 162° C., preferably of maximum 140° C., more preferably of maximum 120° C. in order to facilitate the removal of the product after the transesterification. Examples of acids R$^8$—COOH are formic acid, acetic acid, propionic acid, butyric acid; formic acid and acetic acid with respectively 100° C. and 118° C. as boiling point are preferred. Because of the wider availability of trialkylsilylacetates, these products are most preferred for the process of this invention.

In another embodiment of the invention the acyloxysilanes are derived from partially or totally halogenated acids as defined hereabove, preferably from fluorinated or chlorinated acids, more preferably from trifluoroacetic acid with 72° C. as boiling point The acyloxysilanes (II) for use in the process of the invention are known (see table) or (for higher alkyl groups on the silicium) can be obtained by known methods. Some examples are given in the following table:

| Acyloxysilane | CAS registry number |
| --- | --- |
| Trimethylsilylformiate | 18243-21-5 |
| Trimethylsilylacetate | 2754-27-0 |
| Triethylsilylacetate | 5290-29-9 |
| Trimethylsilyltrifluoroacetate | 400-53-3 |
| Tri-n-propylsilylacetate | 17315-26-3 |
| Tri-n-butylsilylacetate | 22192-48-9 |
| Triisopropylsilyl acetate | 17315-27-4 |
| Trimethylsilylpropionate | 16844-98-7 |
| Trimethysilyltrichloroacetate | 25436-07-1 |
| Tert-butyldimethylsilylacetate | 37170-48-2 |
| Pentamethyl-1-acetoxy-disiloxane | 70693-47-9 |
| Heptamethyl-1-acetoxy-trisiloxane | 3292-96-4 |
| Nonamethyl-1-acetoxy-tetrasiloxane | 3453-81-4 |
| Undecamethyl-1-acetoxy-pentasiloxane | 3560-95-0 |
| Tridecamethyl-1-acetoxy-hexasiloxane | 144139-44-6 |

Examples of the organosilylated carboxylate monomers prepared by the process of the invention using (meth)acrylic acid include trimethylsilyl (meth)acrylate, triethylsilyl (meth)acrylate, tri-n-propylsilyl (meth)acrylate, triisopropylsilyl (meth)acrylate, tri-n-butylsilyl (meth)acrylate, triisobutylsilyl (meth)acrylate, tri-s-butylsilyl (meth)acrylate, tri-n-amylsilyl (meth)acrylate, tri-n-hexylsilyl (meth)acrylate, tri-n-octylsilyl (meth)acrylate, tri-n-dodecylsilyl (meth) acrylate, triphenylsilyl (meth)acrylate, tri-p-methylphenylsilyl (meth)acrylate, tribenzylsilyl (meth)acrylate, tri t-butylsilyl (meth)acrylate.

Other examples include ethyldimethylsilyl (meth)acrylate, n-butyldimethylsilyl (meth)acrylate, bis(trimethylsilyl) itaconate, t-butyl dimethylsilyl (meth)acrylate diisopropyl-n-butylsilyl (meth)acrylate, n-octyldi-n-butylsilyl (meth) acrylate, diisopropylstearylsilyl (meth)acrylate, dicyclohexylphenylsilyl (meth)acrylate, t-butyldiphenylsilyl (meth)acrylate, phenyldimethylsilyl (meth)acrylate, lauryldiphenylsilyl (meth)acrylate, pentamethyl-1-(meth)acryloyloxy-disiloxane, heptamethyl-1-(meth)acryloyloxy-trisiloxane, nonamethyl-1-(meth)acryloyloxy-tetrasiloxane, undecamethyl-1-(meth)acryloyloxy-pentasiloxane, tridecamethyl-1-(meth)acryloyloxy-hexasiloxane.

Examples of organosilylated carboxylate monomers of general formula (I) wherein R$^7$ is the ester of the above-described formula (III) include triisopropylsilyl methyl maleate, triisopropylsilyl amyl maleate, tri-n-butylsilyl n-butyl maleate, t-butyldiphenylsilyl methyl maleate, t-butyldiphenylsilyl n-butyl maleate, triisopropylsilyl methyl fumarate, triisopropylsilyl amyl fumarate, tri-n-butylsilyl n-butyl fumarate, t-butyldiphenylsilyl methyl fumarate, and t-butyldiphenylsilyl n-butyl fumarate.

The advantage of this invention is that the process uses reactants, which can be easily handled. Another advantage lies in the simplicity and safety of the procedure (no filtration of salt neither trapping of corrosive gaseous matter). Furthermore, another advantage is that the reaction may take place without any added catalyst and can be performed under reduced pressure. A further advantage is that the formed carboxylic acid may be removed under azeotropic distillation. Also there is no need to add polymerisation inhibitors and no degradation of the material occurs. Due to its shortness, its easy work-up procedure and its high yield the process of the present invention can be considered as a substantial improvement over the existing methods described above.

Still another advantage of the invention is that the organosilylated carboxylate monomers obtained by the process according to the invention have the exactly desired number of dihydrocarbylsilyloxy units, said number of dihydrocarbylsilyloxy units being those as defined in the acyloxysilane.

The organosilylated carboxylate monomers obtained by the process of the invention can be polymerised with various other monomers such as vinyl monomers including acrylic esters, methacrylic esters, styrene, vinyl esters (e.g., vinyl acetate, vinyl propionate, vinyl butyrate, vinyl benzoate), vinyltoluene, alpha-methylstyrene, crotonic esters, and itaconic esters.

The polymers and copolymers of said monomers are useful in coating or paint composition. More preferably they are used as comonomer unit in the binder of antifouling coating compositions. When used in an antifouling coating composition, they give a film which undergoes neither cracking nor peeling and shows moderate hydrolysability to dissolve into seawater constantly at an adequate rate and which therefore exhibits excellent antifouling property for long term.

The antifouling coating compositions prepared using the monomers obtained by the process of the invention are tin-free coatings and provide an alternative to the present self-polishing coating technology based on hydrolysable tributyl tin polymers (the use of which is due to be banned in antifouling paints by 2003). The organosilylated carboxylate monomers provided by the process of the invention compared to organotin compounds are less toxic, less polar, more hydrophobic and more stable.

EXAMPLES

In the following examples, NMR data have been determined In CDCl3 and are expressed as delta versus TMS.

Example 1

Preparation of Trimethylsilyl Methacrylate 20 ml of acetoxytrimethylsilane and 11.4 ml of commercial methacrylic acid (ATOFINA Norsocryl® MAA) in 100 ml of hexane are mixed and heated. Azeotropic distillation of acetic acid affords trimethylsilyl methacrylate.

Trimethysilyl methacrylate: 13C NMR: 167.7, 137.6, 127.1, 18.2, −0.257; 29 Si NMR: 24.3; IR (film): 2963, 1703, 1335, 1256, 1178, 874, 854 cm−1.

Example 2

Preparation of Tri-n-butylsilyl Methacrylate 4 g of acetoxytri-n-butylsilane and 1.33 g of commercial methacrylic acid (ATOFINA Norsocryl® MAA) are mixed at room temperature, acetic acid is then distilled under reduced pressure (45° C./13 hPa) to afford tri-n-butylsilyl methacrylate.

Tri-n-butylsilyl methacrylate: 13 C NMR: 167.8, 137.9, 126.0, 26.7, 25.5, 18.5, 13.5, 14.0; 29Si NMR: 23.1; IR (film): 2959, 2927, 1703, 1334, 1174, 886, 766 cm-1.

Example 3

Preparation of Nonamethyl-1-methacryloyloxy-tetrasiloxane 5 g of nonamethyl-1-acetoxy-tetrasiloxane prepared as described in reference example of EP-0839869 and 2.31 g of commercial methacrylic acid (ATOFINA Norsocryl® MAA) are mixed at room temperature. Acetic acid is then distilled under reduced pressure (45° C./13 hPa) to afford nonamethyl-1-methacryloyloxy-tetrasiloxane.

Nonamethyl-1-methacryloyloxy-tetrasiloxane: 13C NMR: 166.8, 126.3, 137.8, 18.1, 1.95, 1.24, 1.03, −0.13; 29Si NMR: 7.3, −8.8, −20.1, −21.6; IR (film): 2963, 1730, 1372, 1260, 1083, 1045, 841, 809 cm-1.

Example 4

Preparation of Triisopropylsilyl Acrylate 4 g of acetoxy-triisopropylsilane and 1.6 g of acrylic acid (ATOFINA Norsocryl AA®) in 100 ml of toluene and 1 mL of N,N-dimethylformamide are mixed and heated. Azeotropic distillation of acetic acid affords triisopropylsilyl acrylate.

Triisopropylsilyl acrylate: 13C NMR: 132.5, 130.4, 175.0, 12.3, 17.0; 29Si NMR: 21.84; IR (film): 2948, 2870, 1708, 1620, 1465, 1403, 1290, 1209, 1046, 884, 818, 746 cm−1.

The invention claimed is:

1. Process for the preparation of organosilylated carboxylate monomers of general formula (I)

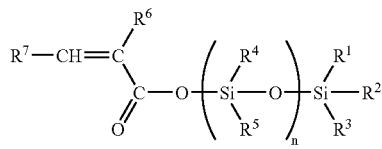

(I)

wherein
$R^1$, $R^2$, $R^3$, $R^4$, $R^5$ each independently represent an alkyl, an aryl group or an hydrogen atom, $R^6$ represents a hydrogen atom or a methyl group or —CH$_2$—COO—(SiR$^4$R$^5$O)n-SiR$^1$R$^2$R$^3$ wherein $R^1$, $R^2$, $R^3$, $R^4$, $R^5$ are as already defined,
$R^7$ represents a hydrogen atom, an alkyl group or —COOR$^9$ wherein $R^9$ represents an alkyl group,
n represents a number of dihydrocarbylsiloxane units from 0 to 200,
which process comprises the steps of reacting:
an acyloxysilane of formula (II)

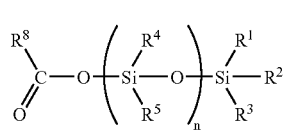

(II)

wherein
$R^1$, $R^2$, $R^3$, $R^4$ and $R^5$ are as already defined above and,
$R^8$ is a hydrogen atom, a $C_1$–$C_3$ alkyl group or a partially or totally hydrogenated $C_1$–$C_3$ alkyl group,
n represents the same number of dihydrocarbylsiloxane units as those defined above in formula (I),
with an unsaturated carboxylic acid of formula (III),

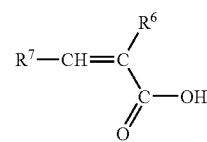

(III)

wherein
$R^6$ is a hydrogen atom or a methyl group or CH$_2$COOH and,
$R^7$ has the same meaning as that defined above.

2. A process according to claim 1, wherein $R^1$, $R^2$, $R^3$, $R^4$, $R^5$ and $R^9$ each independently represent a linear, branched, cyclic alkyl, aryl or substituted aryl group, saturated or unsaturated, containing from 1 to 12 carbon atoms.

3. A process according to claim 2 wherein $R^1$, $R^2$, $R^3$, $R^4$, $R^5$ each independently are chosen from the group of methyl, ethyl, propyl, isopropyl, i-butyl, n-butyl, sec butyl, t-butyl.

4. A process according to claim 1 wherein n represents a number of dihydrocarbylsiloxane unit equal to zero.

5. A process according to claim 4 wherein $R^1$, $R^2$, $R^3$ are n-butyl or isopropyl and equal zero.

6. A process according to claim 1, wherein n represents a number of dihydrocarbylsiloxane units from 1 to 200.

7. A process according to claim 6 wherein $R^1$, $R^2$, $R^3$, $R^4$, $R^5$ are methyl and n is not zero.

8. A process according to claim 1, wherein the unsaturated carboxylic acids of formula (III) is selected from the group of acrylic acid, methacrylic acid, crotonic acid, angelic acid, tiglic acid, maleic acid, fumaric acid, itaconic acid, preferably from acrylic and methacrylic acids.

9. A process according to claim 1, wherein the acyloxysilane of formula (II) is derived from carboxylic acids having a boiling point of maximum 162° C.

10. A process according to claim 1, wherein $R^1$, $R^2$, $R^3$, $R^4$, $R^5$ and $R^9$ each independently represent a linear, branched, cyclic alkyl, aryl or substituted aryl group, saturated or unsaturated, containing from 1 to 6 carbon atoms.

11. A process according to claim 1, wherein $R^1$, $R^2$, $R^3$, $R^4$, $R^5$ and $R^9$ each independently represent a linear, branched, cyclic alkyl, aryl or substituted aryl group, saturated or unsaturated, containing from 1 to 4 carbon atoms.

12. A process according to claim 1, wherein $R^1$, $R^2$, $R^3$, $R^4$, $R^5$ and $R^9$ each independently represent a liner, branched, cyclic alkyl, aryl or substituted aryl group, saturated or unsaturated, containing 4 carbon atoms.

13. A process according to claim 1, wherein the acyloxysilane of formula (II) is derived from carboxylic acids having a boiling point of maximum 140° C.

14. A process according to claim 1, wherein the acyloxysilane of formula (II) is derived from carboxylic acids having a boiling point of maximum 120° C.

* * * * *